United States Patent [19]

Kallok

[11] Patent Number: 5,281,219
[45] Date of Patent: Jan. 25, 1994

[54] MULTIPLE STIMULATION ELECTRODES

[75] Inventor: Michael J. Kallok, New Brighton, Minn.

[73] Assignee: Medtronic, Inc., Minneapolis, Minn.

[21] Appl. No.: 934,030

[22] Filed: Aug. 24, 1992

Related U.S. Application Data

[63] Continuation of Ser. No. 617,158, Nov. 23, 1990, abandoned.

[51] Int. Cl.$^5$ ............................................... A61N 1/36
[52] U.S. Cl. ................................... 607/42; 607/72; 607/2; 607/115
[58] Field of Search ............... 128/421, 419 R, 799, 128/783, 786, 642, 419 D, 419 PG

[56] References Cited

U.S. PATENT DOCUMENTS

| | | | |
|---|---|---|---|
| 3,543,761 | 12/1970 | Bradley | 128/421 |
| 3,646,940 | 3/1972 | Timm et al. | 128/419 E |
| 3,851,651 | 12/1974 | Icenbice, Jr. | 128/422 |
| 3,888,261 | 6/1975 | Maurer | 128/420 R |
| 3,937,226 | 2/1976 | Funke | 128/419 D |
| 4,088,140 | 5/1978 | Rockland et al. | 128/419 D |
| 4,390,023 | 6/1983 | Rise | 128/421 |
| 4,411,268 | 10/1983 | Cox . | |
| 4,414,982 | 11/1983 | Durkan . | |
| 4,457,303 | 7/1984 | Durkan . | |
| 4,462,398 | 7/1984 | Durkan et al. . | |
| 4,484,578 | 11/1984 | Durkan . | |
| 4,506,666 | 3/1985 | Durkan . | |
| 4,559,951 | 12/1985 | Dahl et al. | 128/786 |
| 4,580,570 | 4/1986 | Sarrell et al. | 128/421 |
| 4,628,934 | 12/1986 | Pohndorf et al. | 128/419 PG |
| 4,712,558 | 12/1987 | Kidd et al. | 128/421 |
| 4,830,008 | 5/1989 | Meer . | |
| 4,570,631 | 2/1986 | Durkan . | |
| 4,969,463 | 11/1990 | Dahl et al. | 128/419 D |
| 5,014,705 | 5/1991 | Graupe et al. | 128/423 W |
| 5,020,542 | 6/1991 | Rossmann et al. | 128/421 |

OTHER PUBLICATIONS

"Diaphragm Pacing: Present Status", by Glenn, Pace, vol. 1, pp. 357-370.
"Laryngeal Pacemaker. II Electronic Pacing of Reinnervated Posterior Cricoarytenoid Muscles in the Canine", by Broniuatowski et al., Laryngoscope, 95: Oct. '85.
"Assessment of Muscle Action on Upper Airway Stability in Anesthetized Dogs", by Strohl et al., J. Lab. Clin. Med, vol. 110, No. 2, Aug. 1987.
"The Role of the Tongue in Sleep Apnea", by Harper et al., Sleep Apnea Syndromes, pp. 219-234, Alan R. Liss Inc.
"Motor Prosthesis" by J. T. Morliner, Handbook of Physiolory, Section 1 The Nervous System, vol. 2, Motor Ceadol, Part. I. pp. 178-179.

Primary Examiner—William E. Kamm
Assistant Examiner—Kennedy J. Schaetzle
Attorney, Agent, or Firm—Harold R. Patton; Daniel W. Latham; John L. Rooney

[57] ABSTRACT

A technique for reducing fatigue associated with artificially stimulated contractions of muscle tissue. The stimulation of the muscle tissue is associated with treatment of a particular medical condition, such as obstructive sleep apnea. For this application, the muscles of the upper airway are stimulated to relieve or prevent obstruction to normal respiratory activity during sleep.

Fatigue is reduced by stimulating the subject muscles from multiple rather than a single electrode. This ensures that successive depolarizations are not produced from the same focus, and that different motor units are successively depolarized.

Each electrode is placed at the muscle nerve interface to recruit the assistance of the nerve tissue in conducting the stimulation signals throughout the muscle. The conductors coupling the individual electrodes share a common cable structure to produce ease in the implant procedure. The electronics of the stimulation pulse generator is conveniently demultiplexed to eliminate excess hardware.

8 Claims, 10 Drawing Sheets

MULTIPLE STIMULATION ELECTRODES

This is a continuation of co-pending application Ser. No. 07/617,158 filed on Nov. 23, 1990 now abandoned.

BACKGROUND OF THE INVENTION

1. Field of the Invention

The present invention is generally related to implantable medical devices, and is more particularly related to implantable medical devices for stimulation of skeletal muscles.

2. Description of the Prior Art

Electrical stimulation of muscle tissue associated with respiration has been known as a technique for treatment of respiratory conditions. "Diaphragm Pacing: Present Status", by William W. L. Glenn, in *Pace*, Volume 1, pp. 357-370, (July-September 1978) describes a number of early attempts to correct central sleep apnea with electrical stimulation.

Treatment of obstructive sleep apnea using electrical stimulation has also been discussed. "Laryngeal Pacemaker. II Electronic Pacing of Reinnervated Posterior Cricoarytenoid Muscles in the Canine", by Broniatowski et al, in *Laryngoscope*, Volume 95, pp. 1194-1198 (October 1985); "Assessment of Muscle Action on Upper Airway Stability in Anesthetized Dogs", by Strohl et al., in *Journal of Laboratory Clinical Medicine*, Volume 110, pp. 221-301, (1987); and U.S. Pat. No. 4,830,008 issued to Meer all discuss electrical stimulation of the upper airway to treat obstructive sleep apnea.

However, little attention within the field of muscle stimulation has been expressly directed to muscle fatigue. James A. Cox in U.S. Pat. No. 4,411,268 describes a technique for conditioning skeletal muscles to prevent fatigue. This process occurs over time and is associated with a conditioning stimulation protocol.

SUMMARY OF THE INVENTION

The present invention overcomes the disadvantages of the prior art by providing apparatus for and a method of minimizing fatigue occurring as a result of electrically stimulating muscle tissue. The technique employs multiple electrodes which are used to stimulate multiple sites of a single muscle mass. The electrodes are energized sequentially or in some other pattern which ensures that successive contractions of the muscle motor units are stimulated from different foci. Fatigue is minimized by allowing motor units to rest between successive stimuli, but maintaining tone by always having some motor units firing from these different stimulation foci.

The electronic circuitry coupled to the multiple electrodes can readily demultiplex the output signal to the various different electrodes. This permits the system to employ a minimum of electronic circuitry. The conductors which energize the individual electrodes are preferably cabled into a single structure to promote ease in implantation.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
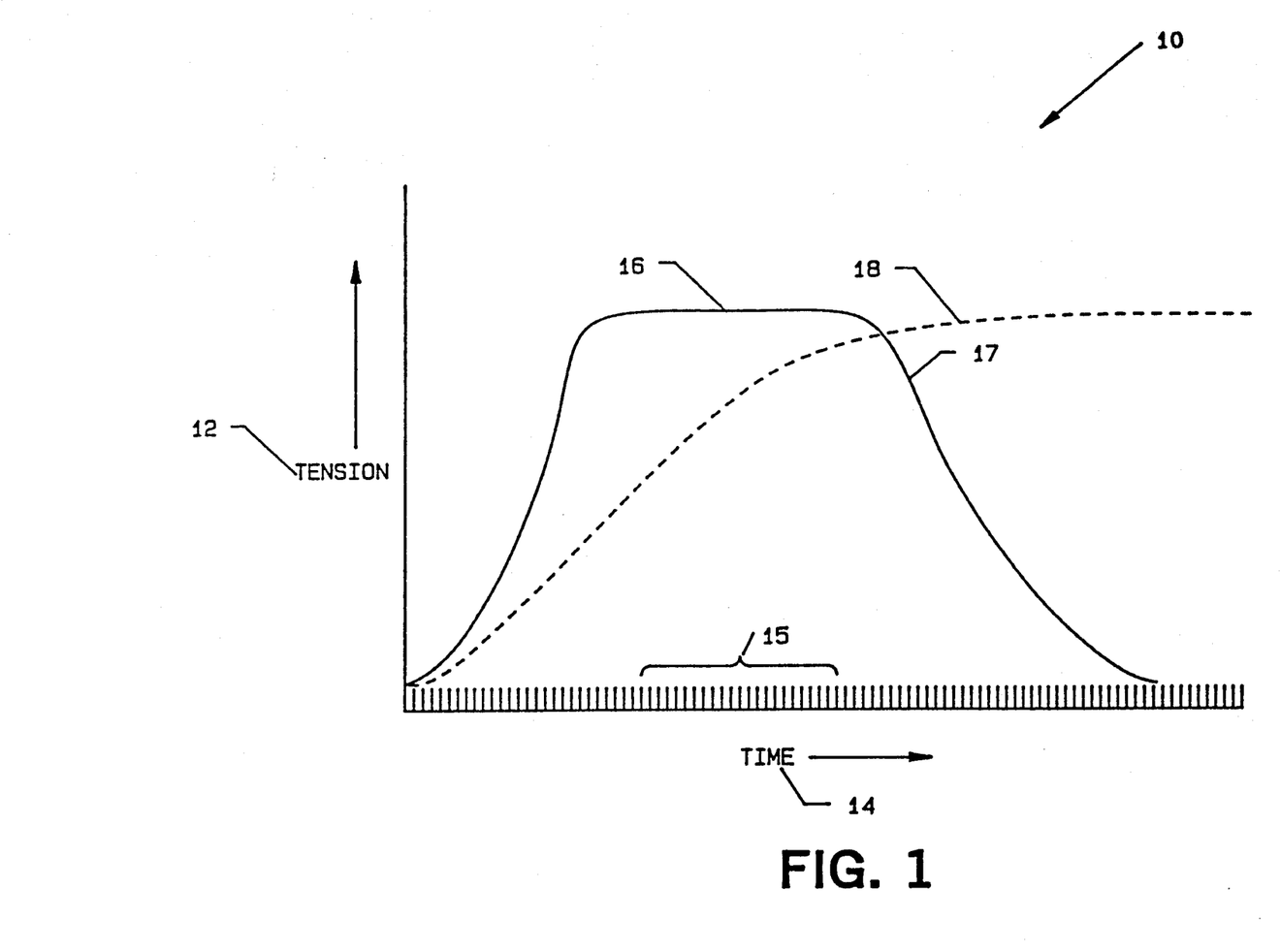
FIG. 1 is a graphical representation of muscle tension as a function of time for two electrode configurations.

FIG. 1 is a graphical representation 10 of muscle tension 12 as a function of time 14 for a single electrode system 16 and a multiple electrode system 18 under chronic stimulation pulses 15. Though this is a conceptualized relationship, it should be clear to the observer that under the single electrode system 16, all motor units are stimulated simultaneously resulting in higher total tension which occurs quickly following the initiation of stimulation. However, stimulation of all motor units simultaneously also results in simultaneous fatigue of all motor units. Tension drops off at point 17, and will remain low until all motor units have rested.

Because the multiple electrode system 18 stimulates different motor units at different times, maximum overall tension is less than that for the single electrode system 16 and is arrived at more slowly. However, the multiple electrode system 18 permits different motor units to rest at different times such that significant tension may be maintained chronically.

For the multiple electrode system 18 having "x" electrodes, each motor unit is stimulated by every "x+1" stimulation pulse. The system may be optimized by choosing x such that a given motor unit has just completed sufficient rest at the delivery of the x+1 stimulation pulse. If x is chosen too small, all motor units will exhibit some chronic fatigue. For an x which is too large, total tension is sacrificed because of the excess number of motor units at rest at any one time.

Figure 2:
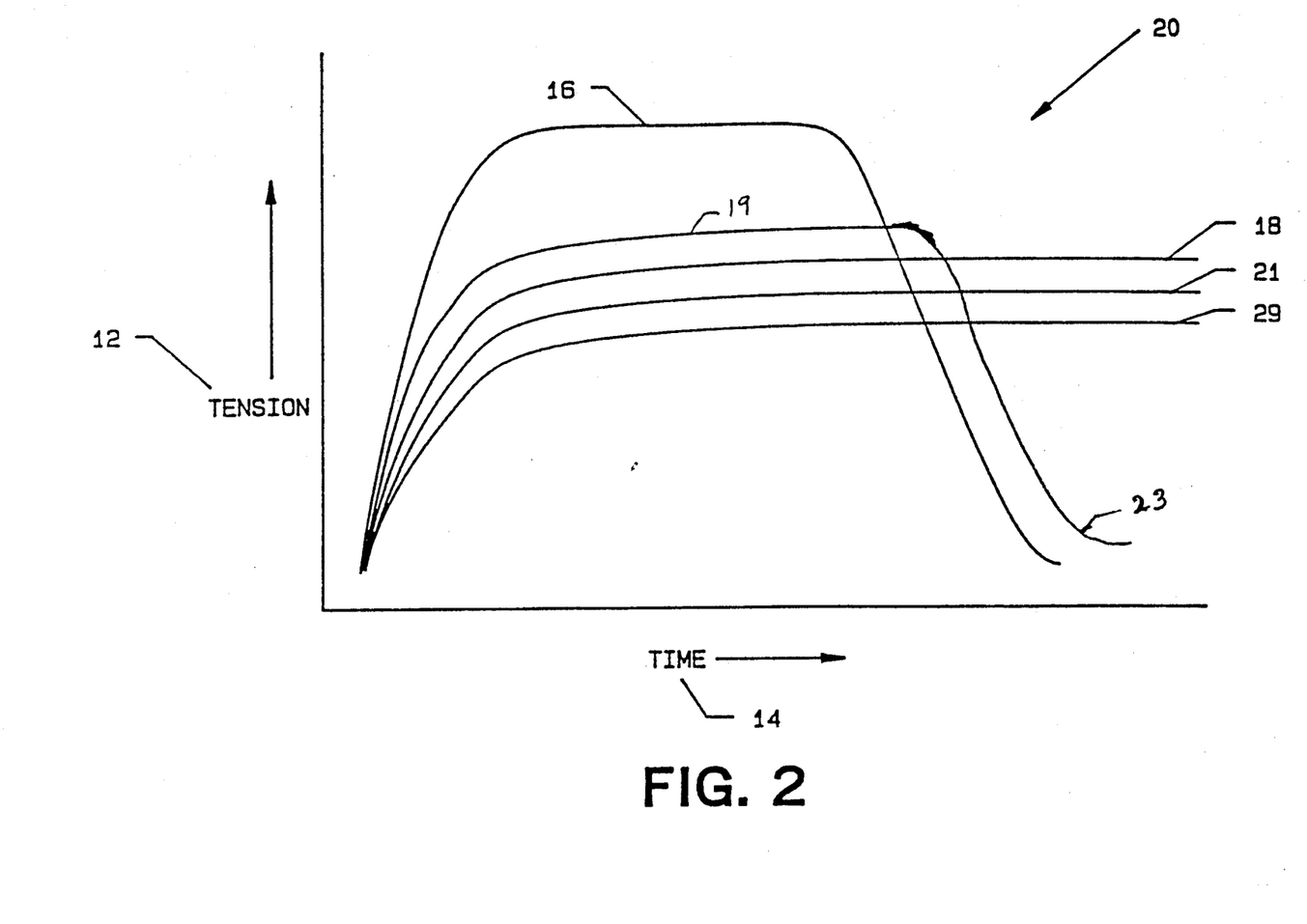
FIG. 2 is a graphical representation of tension as a function of the number of electrodes.

FIG. 2 is a graphical representation 20 of the tension of muscular contraction as a function of time for various numbers. It is assumed in this example that stimulation pulses are applied periodically and with sufficient frequency to cause an observable fatigue effect (see also FIG. 1).

As explained above, single electrode system 16 provides the greatest peak tension, but results in the most pronounced fatigue. Multiple electrode system 19 has an insufficient number of electrodes resulting in chronic fatigue shown at point 23. Multiple electrode systems 21, 18 and 29 have increasing numbers of excess electrodes resulting in lower chronic tension.

Figure 3:
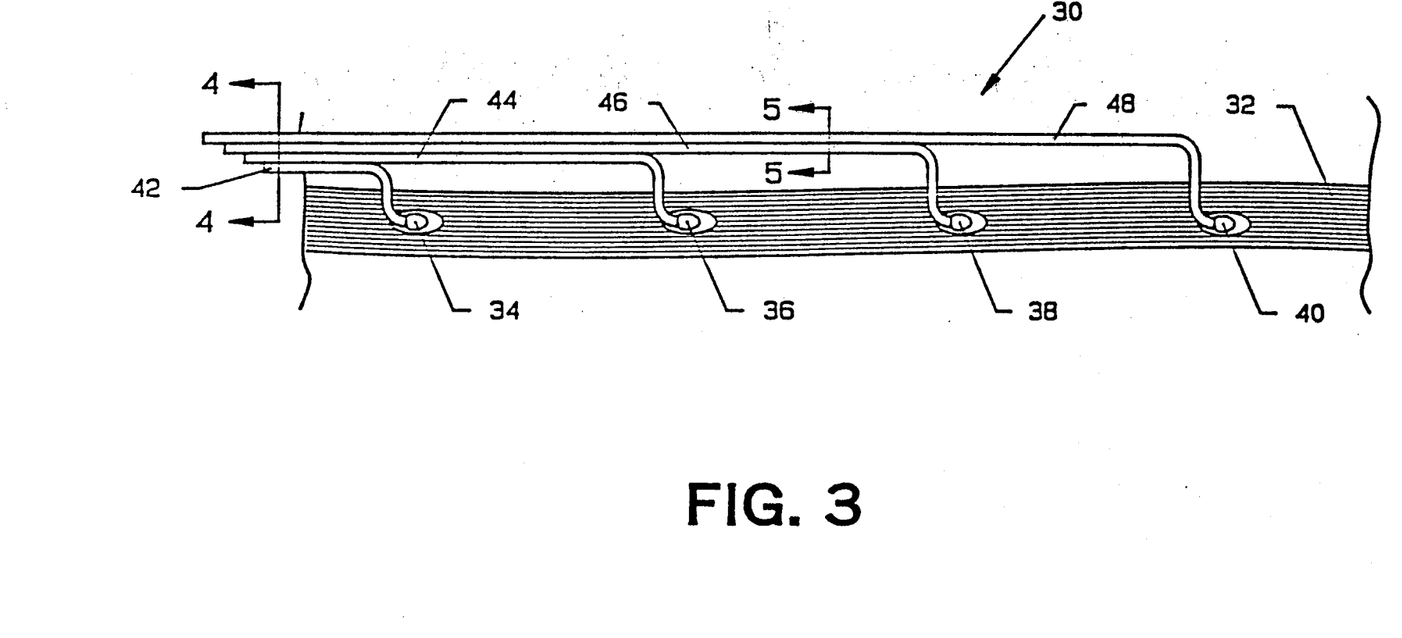
FIG. 3 is a plan view of a plurality of electrodes as coupled to a muscle.

FIG. 3 is a plan view of an electrode system coupled to patient muscle 32. The proximal end of multiple conductor cable 30 is coupled to the implantable stimulation generator (not shown). Insulated lead 42 is coupled to electrode 34. As a preferred embodiment and not intended to be limiting of the present invention, electrode 34 is a stab-in electrode similar to Medtronic ® Model 4951 electrode. In accordance with optimal stimulation practices, electrode 34 should be in direct contact with patient muscle 32 at a point adjacent to the nerve/muscle interface to assist in recruiting the nerve tissue for enhanced communication of the stimulating pulse.

Electrode 36 is coupled to insulated lead 44. Similarly, electrode 38 is coupled to insulated lead 46 and electrode 40 is coupled to insulated lead 48. Each of electrodes 34, 36, 38, and 40 is similar in design and construction. The interelectrode spacing produced by the lengths of the individual insulated leads relative to cable 30 promotes ease of implant.

Figure 4A:
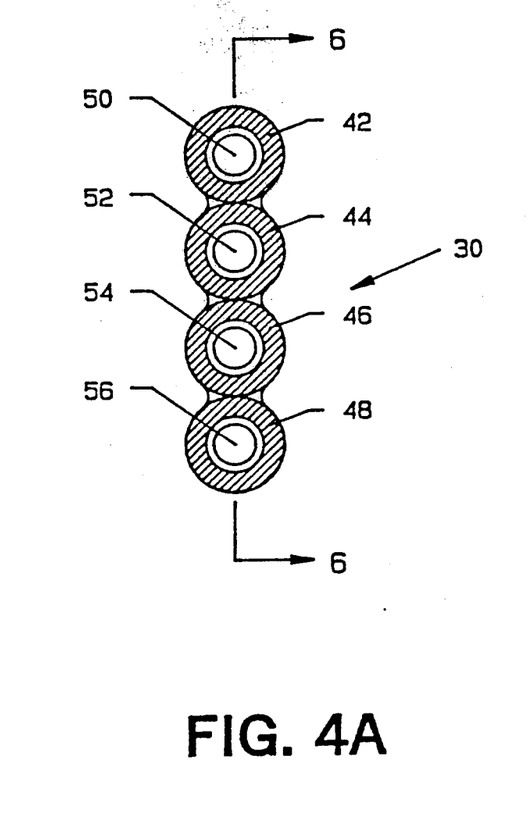
FIG. 4A is a cross-sectional view of a stimulation cable having four conductors.

FIG. 4A is a cross-sectional view of cable 30 showing all four conductors. Insulated lead 42 has inner conductor 50. For chronically implantable systems, inner conductor 50 is preferably a coil of biocompatible wire such as platinum, platinum alloy, silver cored MP35N, or other suitable wire. The insulation may be of silicon rubber or an implantable polymer.

Inner conductors 52, 54, and 56 are similarly constructed. Individual insulated leads 42, 44, 46, and 48 are mechanically coupled as shown for ease of implant.

Figure 4B:
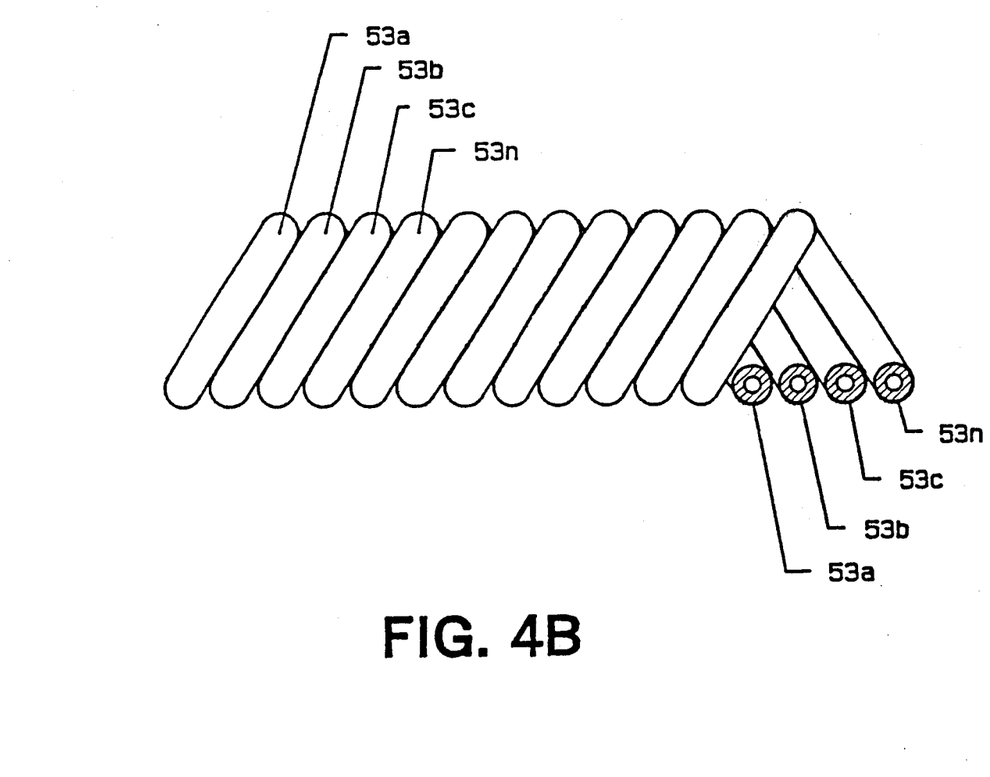
FIG. 4B shows an alternative embodiment of a stimulation cable.

FIG. 4B is a plan view of a portion of an alternative embodiment of a cable for use in practicing the present invention. It uses a multifilar coil 51 of mutually insulated conductors 53a-53n.

Figure 5:
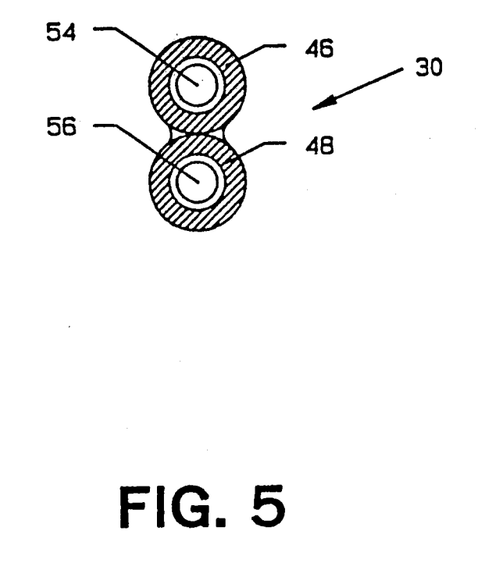
FIG. 5 is a cross-sectional view of a stimulation cable having two conductors.

FIG. 5 is a cross-sectional view of cable 30 taken distal of FIG. 4. All referenced elements are as previously described.

Figure 6:
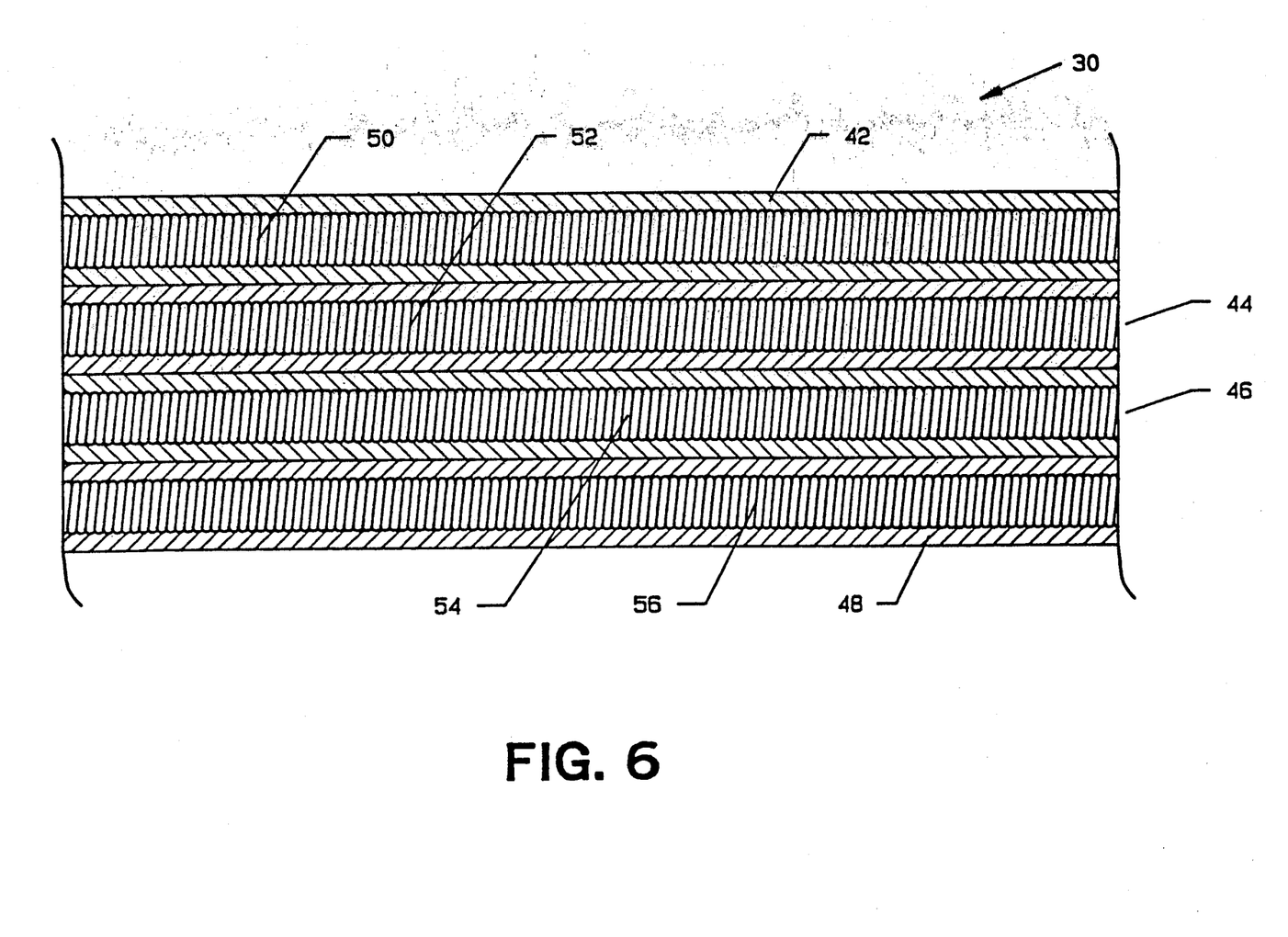
FIG. 6 is a longitudinal sectioned view of a stimulation cable.

FIG. 6 is a longitudinal sectioned view of cable 30. This view shows that inner conductors 50, 52, 54, and 56 are coiled helices.

Figure 7:
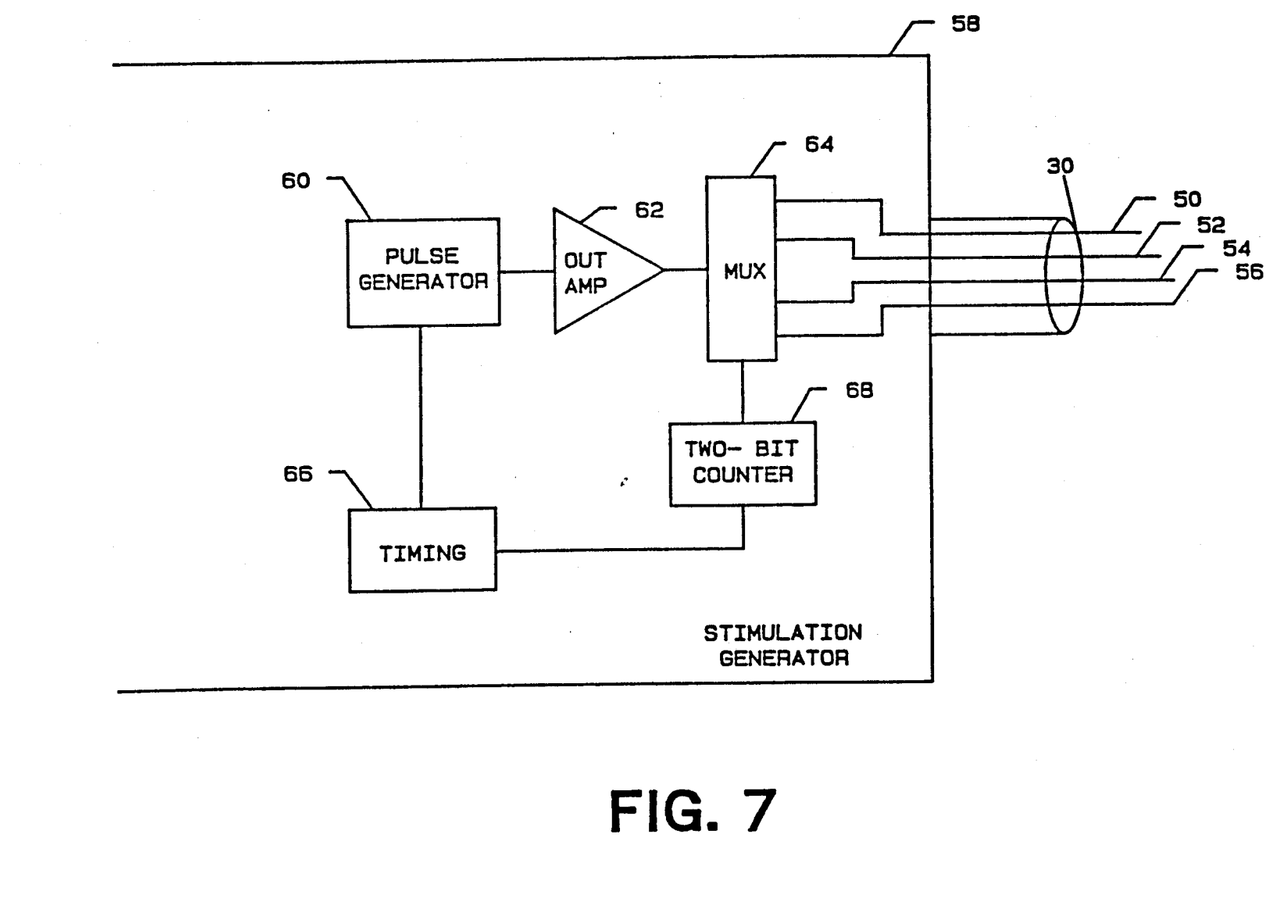
FIG. 7 is a block diagram of the circuitry of the implantable pulse generator.

FIG. 7 is a block diagram of stimulation generator 58. Preferably, stimulation generator 58 is a battery operated device suitable for chronic implantation. It is coupled to the proximal end of cable 30.

Each of inner conductors 50, 52, 54, and 56 is coupled to a different one of the outputs of demultiplexer mux 64. Demultiplexer mux 64 switches sequentially amongst the four conductors thereby routing successive stimulating pulses to different ones of the four electrodes 34, 36, 38, and 40 (see also FIG. 3).

The stimulating pulses are generated by pulse generator 60 and amplified by output amplifier 62. Demultiplexer mux 64 sequentially selects amongst the outputs based upon counter 68 which causes each successive stimulating pulse to be transferred to the next sequential conductor and electrode. Timing 66 ensures that demultiplexer mux 64 and pulse generator 60 are operated synchronously.

Figure 8:
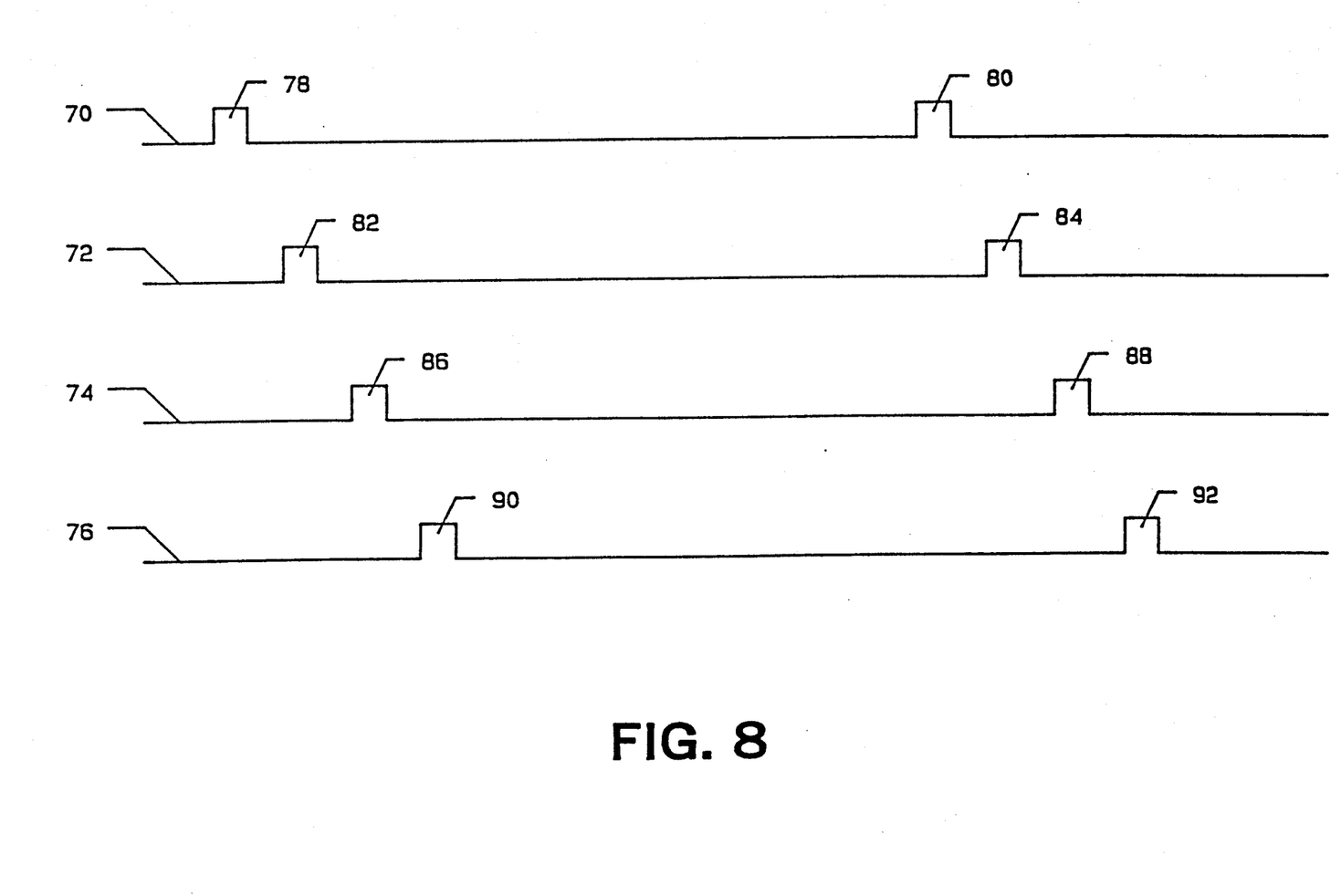
FIG. 8 is a graphical representation of the sequential stimulation pulses.

FIG. 8 is a graphical representation of the output of stimulation generator 58. Wave form 70 represents the output to inner conductor 50, and therefore, the stimulation signal applied to electrode 34. Stimulation pulses 78 and 80 are thus used to stimulate muscle 32 from electrode 34 (see also FIG. 3).

Wave form 72 showing stimulation pulses 82 and 84 is applied to inner conductor 52 and thereby to electrode 36. Similarly, pulses 86 and 88 of wave form 74 are applied to inner conductor 54 and electrode 38, and pulses 90 and 92 of wave form 76 are applied to inner conductor 56 and electrode 40.

Figure 9:
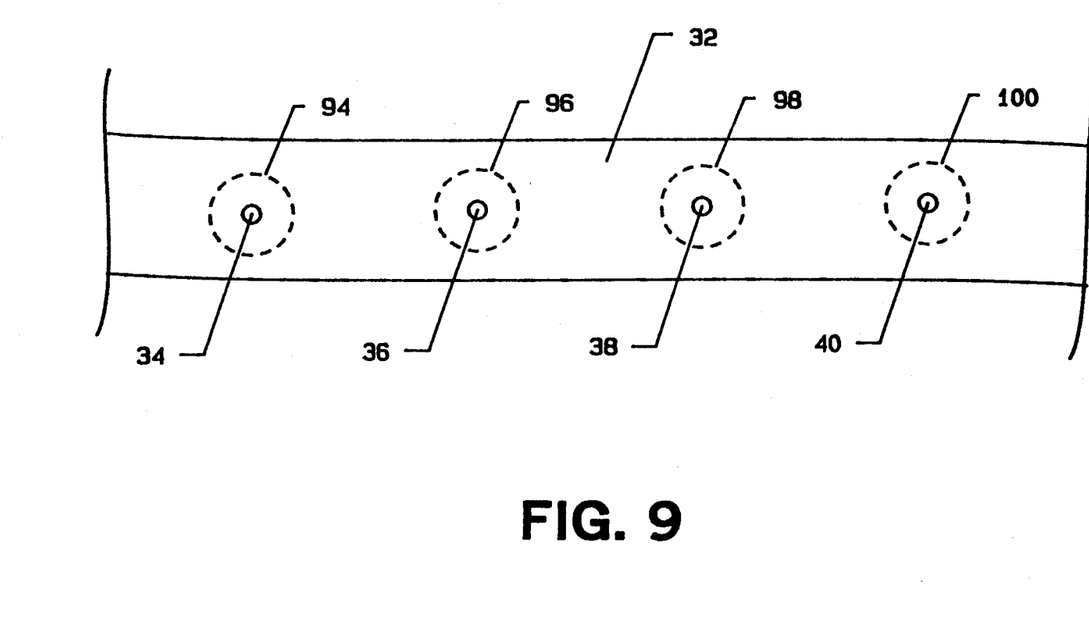
FIG. 9 is a conceptual view of successive contractions stimulated from different foci.

FIG. 9 is a conceptual view of muscle 32 as it is stimulated to depolarize from the foci associated with the various electrodes. Stimulation pulses 78 and 80 (see also FIG. 8) are conducted to electrode 34 and emanate forth as wave front 94. Similarly, stimulation pulses to electrodes 36, 38, and 40 emanate forth on wave fronts 96, 98, and 100, respectively.

Having thus described the preferred embodiments of the present invention, those of skill in the art will be able to readily recognize that yet additional embodiments may be practiced in accordance with the teachings found herein within the scope of the claims hereto attached.

| | |
|---|---|
| 10 | graphical representation |
| 12 | muscle tension |
| 14 | time |
| 15 | chronic stimulation pulses |
| 16 | single electrode system |
| 17 | point |
| 18 | multiple electrode system |
| 19 | multiple electrode system |
| 20 | graphical representation |
| 21 | multiple electrode system |
| 22 | muscular contraction |
| 23 | multiple electrode system |
| 29 | multiple electrode system |
| 30 | cable |
| 32 | patient muscle |
| 36 | electrode |
| 38 | electrode |
| 40 | electrode |
| 42 | insulated lead |
| 44 | insulated lead |
| 46 | insulated lead |
| 48 | insulated lead |
| 50 | inner conductor |
| 51 | multifilar coil |
| 52 | inner conductor |
| 53a-n | insulated conductors |
| 54 | inner conductor |
| 56 | inner conductor |
| 58 | stimulation generator |
| 60 | pulse generator |
| 62 | output amplifier |
| 64 | demultiplexer mux |
| 66 | timing |
| 68 | counter |
| 70 | wave form |
| 72 | wave form |
| 74 | wave form |
| 76 | wave form |
| 78 | stimulation pulse |
| 80 | stimulation pulse |
| 82 | stimulation pulse |
| 84 | stimulation pulse |
| 86 | pulse |
| 88 | pulse |
| 90 | pulse |
| 92 | pulse |
| 94 | wave front |
| 96 | wave front |
| 98 | wave front |
| 100 | wave front |

We claim:

1. An apparatus for stimulating contractions of a muscle with reduced fatigue comprising:
   a. means for providing a train of stimulation pulses at a rate sufficient to produce contraction of said muscle;
   b. a first electrode for electrical coupling to said muscle at a first location;
   c. a second electrode for electrical coupling to said muscle at a second location; and d. conducting means coupled to said means for providing a train of stimulation pulses, to said first electrode, and to said second electrode, for conducting one pulse of said train of stimulation pulses to said first electrode and for conducting any next pulse of said train of stimulation pulses to said second electrode, without regard to the timing relationship between said one and next stimulation pulses.

2. An apparatus according to claim 1 further comprising a plurality of additional electrodes for electrical coupling to said muscle and said conducting means.

3. An apparatus according to claim 2 wherein said conducting means comprises a demultiplexer for switching each sequential pulse of said train of stimulation pulses to a next one of said first electrode, said second electrode, and said plurality of additional electrodes, all without regard to the timing relationship between any sequential stimulation pulses.

4. An apparatus according to claim 3 wherein said conducting means further comprises insulated cable conducting means for transferring said each sequential pulse of said train of stimulation pulses to said next one of said first electrode, said second electrode, and said plurality of additional electrodes.

5. An apparatus according to claim 4 wherein said plurality of electrodes is sufficiently large in number that said stimulation pulses coupled to any individual one of said electrodes are not at a rate sufficient to cause sustained contraction.

6. An apparatus according to claim 5 wherein said insulated conducting cable means comprises a helical coil of conducting wire for each of said plurality of electrodes.

7. A method for reducing fatigue of a muscle undergoing stimulation comprising:
   a. electrically coupling a plurality of electrodes to said muscle;
   b. generating a series of stimulation pulses at a rate sufficient to cause contraction of said muscle; and
   c. coupling different individual pulses of said series of stimulation pulses to different electrodes of said plurality of electrodes, without regard to the timing relationship between said different individual pulses.

8. A method according to claim 7 wherein said coupling step further comprises switching each next sequential pulse of said series of stimulation pulses to a different next sequential electrode of said plurality of electrodes.

* * * * *